United States Patent [19]

Ward

[11] Patent Number: 4,599,471

[45] Date of Patent: Jul. 8, 1986

[54] METHOD FOR OXYGEN ADDITION TO OXIDATIVE REHEAT ZONE OF HYDROCARBON DEHYDROGENATION PROCESS

[75] Inventor: Dennis J. Ward, South Barrington, Ill.

[73] Assignee: UOP Inc., Des Plaines, Ill.

[21] Appl. No.: 776,282

[22] Filed: Sep. 16, 1985

[51] Int. Cl.⁴ .................. C07C 5/333; C07C 5/32
[52] U.S. Cl. .................. 585/441; 585/443; 585/445; 585/655; 585/658; 585/659
[58] Field of Search ........... 585/441, 443, 444, 445, 585/655, 658, 659

[56] References Cited

U.S. PATENT DOCUMENTS

| | | | |
|---|---|---|---|
| 2,416,255 | 4/1947 | Frey | 585/659 |
| 2,465,016 | 3/1949 | Frey | 585/659 |
| 3,409,689 | 11/1968 | Ward | 585/441 |
| 3,437,703 | 4/1969 | Reitmeier et al. | 585/443 |
| 3,502,737 | 3/1970 | Ghublikian | 585/441 |
| 3,515,766 | 6/1970 | Root et al. | 585/402 |
| 3,855,330 | 12/1974 | Mendelsohn et al. | 585/441 |
| 3,904,703 | 9/1975 | Lo et al. | 585/441 |
| 4,292,455 | 9/1981 | Bartek et al. | 585/443 |
| 4,376,225 | 3/1983 | Vora | 585/659 |

FOREIGN PATENT DOCUMENTS 6135427  10/1981  Japan .................. 585/441

*Primary Examiner*—Andrew H. Metz
*Assistant Examiner*—A. Pal
*Attorney, Agent, or Firm*—Thomas K. McBride; John F. Spears, Jr.

[57] ABSTRACT

Hydrocarbons are catalytically dehydrogenated in a reaction zone comprising at least two separate beds of dehydrogenation catalyst. The reactants are reheated and hydrogen is consumed through use of an intermediate bed of hydrogen selective oxidation catalyst. The amount of hydrogen consumed in the combustion step is increased by cooling the effluent of the first dehydrogenation catalyst bed by direct or indirect heat exchange.

18 Claims, 1 Drawing Figure

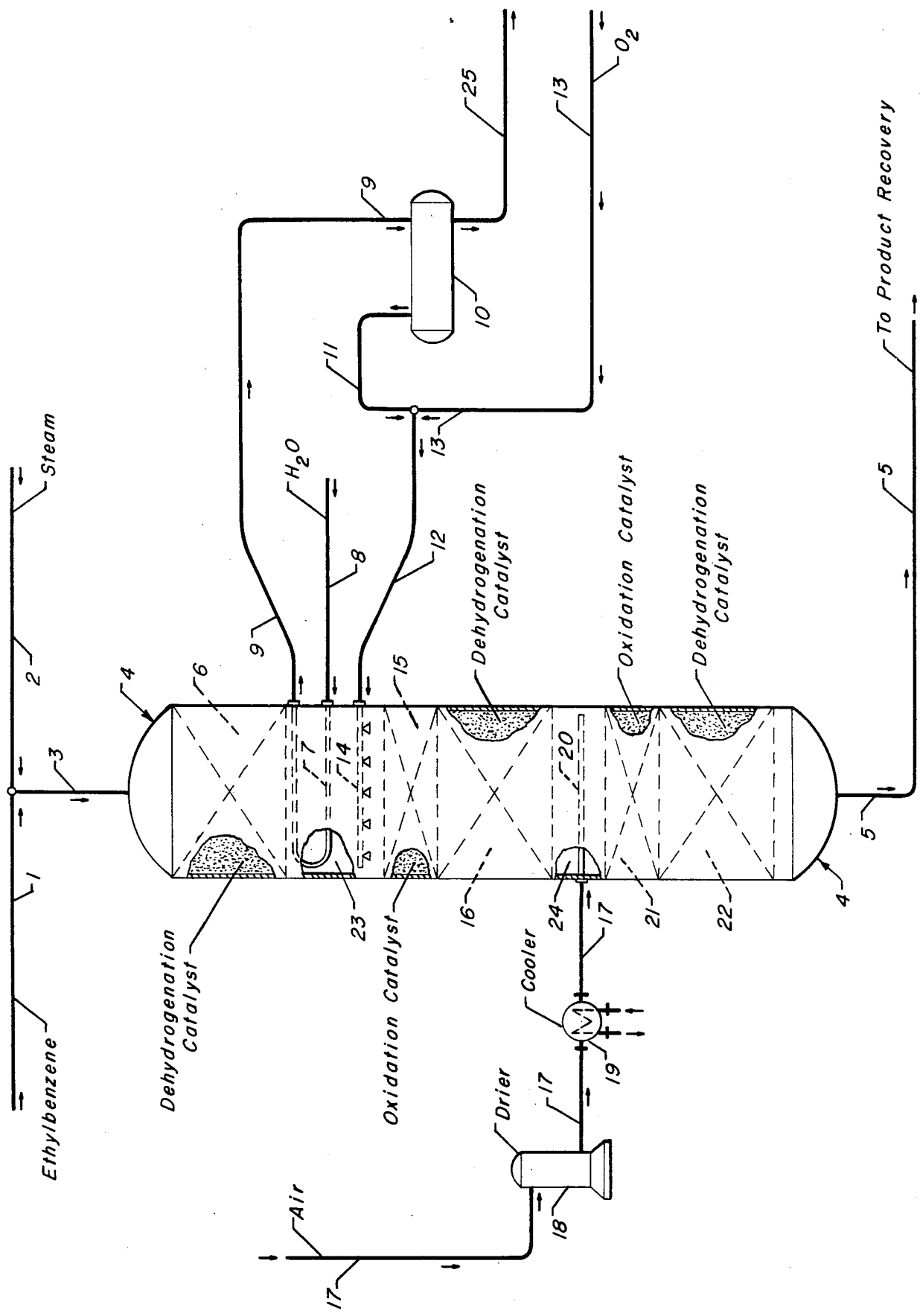

METHOD FOR OXYGEN ADDITION TO OXIDATIVE REHEAT ZONE OF HYDROCARBON DEHYDROGENATION PROCESS

FIELD OF THE INVENTION

The invention relates to the general area of hydrocarbon conversion processes. In particular, the invention relates to a process for the catalytic dehydrogenation of hydrocarbons. The preferred use of the subject method is in the dehydrogenation of alkylaromatic hydrocarbons such as the conversion of ethylbenzene to styrene. The invention is specifically related to the injection of an oxygen-containing gas into beds of a selective hydrogen oxidation catalyst used in the dehydrogenation zone.

PRIOR ART

The dehydrogenation of hydrocarbons is well described in the prior art, with both acyclic and aromatic hydrocarbons being thereby converted to the corresponding less saturated products. For instance, dehydrogenation is performed commercially for the production of styrene from ethylbenzene to fulfill the sizable demand for this polymer precursor. U.S. Pat. No. 3,515,766 issued to W. N. Root et al and U.S. Pat. No. 3,409,689 issued to D. J. Ward are pertinent for their showing of typical prior art catalytic steam dehydrogenation processes for alkylaromatics including ethylbenzene. These references describe the admixture of superheated steam into the feed hydrocarbon and the admixture of additional amounts of superheated steam with the reactants between sequential beds of dehydrogenation catalyst to reheat the reactants.

It is also known in the prior art to pass oxygen into a dehydrogenation zone for the purpose of reacting the oxygen with hydrogen released during the dehydrogenation reaction to thereby liberate heat and to consume hydrogen. The processes known to employ this technique utilize a hydrogen oxidation catalyst in an attempt to selectively oxidize the hydrogen rather than feed or product hydrocarbons also present in the dehydrogenation zone. For instance, U.S. Pat. No. 3,437,703 issued to R. E. Reitmeier et al discloses a dehydrogenation process which may utilize either a "homogeneous catalyst system" in which oxidation and dehydrogenation catalysts are admixed or a layered system of individual catalyst beds referred to as a "multibed" system. Similarly, U.S. Pat. No. 3,855,330 issued to J. C. Mendelsohn et al discloses a dehydrogenation process using sequential beds of dehydrogenation catalyst and oxidation catalyst. It is taught in this reference that it is desirable that oxygen does not come into contact with the dehydrogenation catalysts, and that the major part or all of the added oxygen should be consumed within the bed of oxidation catalyst.

U.S. Pat. No. 3,502,737 issued to J. R. Ghublikian presents a process for the dehydrogenation of ethylbenzene which indicates catalyst activity and stability are maintained by the careful control of the amount of oxygen which is present and by a reduction in the steam which is used in the reaction zone. An oxygen-containing gas such as air is supplied both initially and at interstage points in a carefully controlled manner. It is believed that the teaching of this reference is limited to the use of a catalyst system comprising a physical admixture of the hydrogen oxidation catalyst and the dehydrogenation catalyst, with the presence of oxygen being credited with assisting in the prevention of carbon deposits on the surface of catalytically active sites of the dehydrogenation catalyst.

It is believed that there has heretofore been no attempt or description of increasing the amount of hydrogen consumed in a separate bed of oxidation catalyst by cooling the reactant stream and thereby increasing the amount of heat which must be generated in the oxidation catalyst bed used to heat the reactant stream. The cited references appear silent in this respect. It must be noted that the previously cited patent to R. E. Reitmeier specifies (at column 3, line 50) that an ambient temperature air stream is employed to supply oxygen to a dehydrogenation reactor. This air would cause some cooling when admixed into a dehydrogenation catalyst effluent stream. The reference, however, employs in the example a physical admixture of dehydrogenation and oxidation catalysts such that no beneficial effect can be achieved in the manner of the subject invention. The reference also states it is preferred to admix steam or nitrogen into the oxygen-containing gas streams.

BRIEF SUMMARY OF THE INVENTION

The subject invention provides a means of increasing the per pass conversion which may be achieved in a catalytic dehydrogenation process which employs selective hydrogen combustion to supply interstage reheating. The invention increases the amount of hydrogen which is consumed in the selective hydrogen combustion and thereby lowers the hydrogen concentration experienced in the downstream dehydrogenation catalyst bed(s). The equilibrium is therefore shifted to favor the production of an additional amount of the product dehydrogenated hydrocarbon at otherwise equal conditions. The increased amount of hydrogen-combustion is made necesary by the unique cooling step of the subject process in which the effective effluent of the upstream dehydrogenation zone is cooled as by indirect heat exchange.

One broad embodiment of the invention may accordingly be characterized as a dehydrogenation process which comprises the steps of passing a feed stream comprising the $C_3$-plus feed hydrocarbon into a dehydrogenation zone and through a first bed of dehydrogenation catalyst maintained at dehydrogenation conditions and producing a first dehydrogenation zone effluent stream comprising hydrogen, the $C_3$-plus feed hydrocarbon and a $C_3$-plus product hydrocarbon; cooling the dehydrogenation zone effluent stream by indirect heat exchange, and admixing an oxygen-containing gas stream into the dehydrogenation zone effluent stream; passing the dehydrogenation zone effluent stream into a separate bed of hydrogen selective oxidation catalyst and producing an oxidation zone effluent stream; passing the oxidation zone effluent stream through a second bed of dehydrogenation catalyst maintained at dehydrogenation conditions and producing a second dehydrogenation zone effluent stream which comprises the product hydrocarbon; and recovering the product hydrocarbon.

BRIEF DESCRIPTION OF THE DRAWING

The drawing shows the use of different embodiments of the invention in a process for the dehydrogenation of ethylbenzene. The effluent of dehydrogenation bed 6 is cooled by indirect heat exchanger 7 before being reheated, while cooled air from line 17 is employed to cool the effluent of a second dehydrogenation bed 16 before the reactants enter the oxidation catalyst bed 21.

DETAILED DESCRIPTION

Processes for the dehydrogenation of aromatic hydrocarbons are in a widespread commercial use. For instance, large quantities of styrene are produced by the dehydrogenation of ethylbenzene. The resultant styrene may be polymerized with itself or it may be copolymerized with butadiene, isoprene, acrylonitrile, etc. Other hydrocarbons which may be dehydrogenated in much the same manner include diethylbenzene, ethyl toluene, propylbenzene, and isopropylbenzene. The subject process can also be applied to the dehydrogenation of other types of hydrocarbons including relatively pure or mixed streams of $C_2$-$C_{16}$ paraffins. The process can therefore be applied to the dehydrogenation of propane, butanes, hexanes or nonanes. However, since the great majority of the present commercial dehydrogenation processes are employed for the dehydrogenation of ethylbenzene, the following description of the subject invention will be presented primarily in terms of the dehydrogenation of ethylbenzene. This is not intended to exclude from the scope of the subject invention those alkylaromatic and acyclic hydrocarbons set out above or those having different ring structures including bicyclic compounds.

The dehydrogenation reaction is highly endothermic. Therefore, passing the reactants through a dehydrogenation catalyst bed results in a decrease in the reactant temperature. The endothermicity of the reaction is such that the temperature decrease removes the reactants from the desired temperature range. The reactants are actually cooled to such an extent that the desired reaction does not progress any further at a commercially feasible rate. The desired or commercially necessary per pass conversion therefore cannot be achieved by simply passing the reactants into contact with a single bed of dehydrogenation catalyst. For this reason, it has become standard commerical practice to in some manner perform interstage reheating. In interstage reheating the reactant effluent of a first bed of catalyst is heated to the desired inlet temperature of a second downstream bed of catalyst. This reheating can be performed through direct heat exchange as by the admixture of high temperature steam into the reactant stream emerging from the first catalyst bed. This accomplishes the desired heating, but has a number of drawbacks including the utilities cost of producing the high temperature steam. It also increases the amount of steam which must be condensed to recover the product alkylaromatic hydrocarbons from the effluent stream and increases the total amount of material flowing through the reaction zone, thereby making it more difficult to maintain desired low pressures within the reaction zone.

Another method of interstage reheating comprises the use of indirect heat exchange. In this method the effluent from a dehydrogenation zone is passed through a heat exchanger in which it is heated, and the reactants are then passed into the subsequent dehdyrogenation zone. The high temperature fluid employed in this indirect heat exchange method may be high temperature steam, combustion gases, a high temperature process stream or other readily available high temperature fluids. This method of interstage heating does not dilute the reactants but does impose some pressure drop in the system and can expose the reactants to undesirably high temperatures.

A third method of interstage heating is the oxidative reheat method. This is a newer method which it is believed has not been employed commercially. The driving force for employing the oxidative reheat method is the recognition that the combustion of the hydrogen generated in the dehydrogenation process performs two functions which are beneficial in the dehydrogenation process. First, the consumption of the hydrogen is beneficial in shifting the equilibrium of the dehydrogenation reaction to favor increased amounts of dehydrogenation. Second, the combustion of the hydrogen will release heat sufficient to reheat the reactants to the desired dehdyrogenation conditions. The oxidation is preferably accomplished in the presence of a catalyst which selectively promotes the oxidation of hydrogen as compared to the destructive combustion or oxidation of the more valuable feed and product hydrocarbons. The selective combustion method of interstage reheating presents a more economical dehydrogenation process. It is therefore expected that oxidative reheat will to a significant extent supplant indirect heat exchange as a method of performing the required interstage heating. Therefore, a large number of existing alkylaromatic dehydrogenation process units will be converted from indirect heat exchange to oxidative reheat interstage heating. It is an objective of the subject invention to provide an improved method for oxidative reheating in dehydrogenation process units. It is also an objective of the subject invention to provide a method for increasing the conversion which may be achieved during a single passage through the total reactor sequence of alkylaromatic dehydrogenation process units.

Despite the advances which have been achieved in the arts of catalysis and hydrocarbon conversion, the ultimate conversion which can be achieved during a single passage through an overall dehydrogenation zone is limited to an amount less than total conversion. That is, it is impossible to achieve a 100% conversion of a feed hydrocarbon to a corresponding product dehydrogenated hydrocarbon. A basic limitation in the degree of conversion which may be achieved in any dehydrogenation processes is the equilibrium concentration of the various reactants at the temperatures employed. The effluent stream of a catalytic dehydrogenation zone will therefore comprise an admixture of the feed hydrocarbon and the product hydrocarbon and hydrogen. It is necessary to separate and recovery the product hydrocarbon and to recycle the unconverted feed hydrocarbon. The greater the rate of conversion which is achieved in the dehydrogenation zone, the smaller the amount of unconverted material which must be recycled becomes. The separation of the product and unreacted hydrocarbons requires extensive capital equipment and consumes large amounts of utilities in the form of heat and electrical power. It is therefore desirable to increase the conversion which is achieved per pass in the dehydrogenation zone and to thereby decrease the amount of material which must be separated and recycled through the reactor. A higher per passage conversion will also allow a smaller reaction zone to be employed in the process with the associated reduction in the cost of the reactors, catalyst and utilities cost of operating the reaction zone. For these reasons, it is highly desirable to achieve increased rates of total conversion during the passage of the dehydrogenation zone feed stream through a multibed dehydrogenation reaction zone.

The subject process increases the conversion which is achieved in one pass of the reactants through such a multibed reaction zone. The subject process effects this improvement by consuming a greater amount of the product hydrogen within the oxidation zone and thus shifting the equilibrium concentration in a manner which promotes a greater conversion of the feed hydrocarbons. That is, in the subject process hydrogen is consumed within the reaction zone to a greater extent than in the previously cited references. Therefore, the equilibrium concentration of the product dehydrogenated compound is increased and it is easier to approach a preselected concentration of the product hydrocarbon in the effluent stream than in the prior art references. The overall maximum conversion which can be achieved in the subject process will also exceed that of the previously cited processes.

The improvement of the subject process results from a cooling of the effective effluent stream of an upstream dehydrogenation catalyst bed prior to its passage into the downstream bed of oxidation catalyst employed to reheat the reactant stream. The term "effective effluent stream" is used herein in recognition of the fact that the admixture of the oxygen-containing stream into the actual effluent of the dehydrogenation zone results in a new stream and in that the temperature of this stream may be less than the temperature of the actual effluent stream of the dehydrogenation catalyst bed. That is, the subject invention includes the step of cooling this gas mixture to a lower temperature than results from the admixture of the dehydrogenation zone effluent stream with the oxygen-containing gas stream of the previously described technology. The subject process employs a greater degree of cooling as described more fully below. This greater degree of cooling results in a lower temperature for the gas phase entering the bed of oxidation catalyst than would the admixture of the normal amount of "ambient" air into the effluent stream of the upstream dehydrogenation catalyst bed. The term ambient is used herein in its normal sense of referring to the temperature of air or another material normally present at the process site. Ambient temperature is therefore the same as the daily air temperature experienced at the plant site.

Cooling the effluent stream of the dehydrogenation zone to a lower temperature requires more heat to be generated in the bed of oxidation catalyst. Therefore, more hydrogen must be combusted and more oxygen or air must be added to the process. The larger amount of combustion results in a larger amount of hydrogen being consumed within the bed of oxidation catalyst. The concentration of hydrogen in the effluent stream of the oxidation catalyst bed is therefore reduced as compared to the previously cited references. The heating which is effected within the oxidation catalyst bed would therefore normally be greater than 100 Centigrade degrees and is preferably greater than 120 Centigrade degrees. This increased combustion should consume at a minimum 50 mole percent of the hydrogen which enters the particular bed of oxidation catalyst. Preferably over 75 percent of the entering hydrogen is consumed and more preferably over 85 percent of the entering hydrogen is consumed in the combustion step of the process.

There are many ways in which the cooling step of the subject process may be performed. The cooling step may be performed by direct heat exchange in which the effluent of the dehydrogenation zone is admixed with a low temperature cooling media which may be a gas or a liquid phase stream. Preferably, the direct cooling method at least partially employs the oxygen-containing gas stream as a portion of the cooling media. Air withdrawn from the atmosphere and then cooled as by refrigeration is a preferred coolant. The other basic variation of the cooling step of the subject process is the use of indirect heat exchange. In indirect heat exchange, the effluent of the dehydrogenation catalyst bed is cooled by the transfer of heat through a heat exchange surface into a cooling media circulating through a heat exchanger. This requires no physical admixture of the effluent stream with the cooling media.

It is also possible to practice the subject process using a combination of direct and indirect heat exchange. In this latter variation, it is possible to employ different cooling medias for the direct and indirect heat exchange steps or to employ a single media, such as water which may be vaporized by the indirect heat exchange and then admixed as relatively low temperature steam to effect direct heat exchange and cooling. It is also within the scope of the subject invention that the heat removed by indirect heat exchange could be employed within the process for other purposes such as the generation of steam fed to the first bed of dehydrogenation zone. The heat removed by indirect heat exchange could also be used to heat or vaporize the reactants being charged to the process, for the generation of energy, for the heating of various process streams used in the dehydrogenation process or in another process or to supply heat to a fractionation or other separatory zone which requires an input of heat.

In the oxidative reheat process, an oxygen-containing gas stream is admixed with the effluent of a preceding dehydrogenation zone and the resulting admixture is passed into a bed of selective hydrogen oxidation catalyst. To achieve the optimum levels of performance and safety in this process, it is necessary to closely control the rate at which oxygen is passed into the process in this manner. An insufficient amount of oxygen will result in a less than desired consumption of hydrogen and more importantly a less than desired reheating of the reactant stream. The result will be a decrease in the degree of dehydrogenation achieved during passage through the overall reaction zone. It is not normally desired to inject an excess amount of oxygen into any part of the dehydrogenation zone above that required to perform the desired degree of hydrogen combustion. More specifically, in a normal operation which does not employ the subject process no more than 60 mole percent of the net hydrogen produced in the preceding dehdyrogenation zone need be combusted to achieve a desired degree of reheating.

The passage of an excess amount of oxygen into the dehydrogenation zone will also have detrimental effects upon the long term operation of the process. For instance, oxygen will normally serve to deactivate or poison some commercially employed dehydrogenation catalyst. It is therefore undesirable to have residual oxygen emerging from the oxidation catalyst bed and thereupon contacting dehydrogenation catalyst. Operation of the dehdyrogenation zone in a manner which does not result in the total consumption of the oxygen is also undesirable because of the obvious explosive nature of oxygen-hydrocarbon mixtures. The explosive nature of these mixtures can, however, be essentially negated by properly operating the process to avoid the presence of mixtures being within the explosive range, as through the use of diluents and intentionally low oxygen addition rates, and the presence of a sufficient amount of solid material to act as a explosion suppression means. Lastly, the presence of oxygen is not normally desired in vessels containing hydrocarbons as the oxygen may react with the hydrocarbons to form various undesired oxygenated compounds.

The drawing illustrates the application of several different methods of cooling to a process for the dehydrogenation of ethylbenzene. In this process, a feed stream comprising relatively high purity ethylbenzene carried by line 1 is admixed with superheated steam from line 2 and passed into the dehydrogenation zone 4 through line 3. The feed admixture enters a first bed of dehydrogenation catalyst 6 in which a portion of the ethylbenzene is dehydrogenated to produce styrene and hydrogen. The endothermic dehydrogenation reaction results in a reduction in temperature of the reactant stream as it passes through the dehydrogenation catalyst bed 6. The effluent stream of the catalyst bed 6 enters a void cylindrical volume 23 employed for the cooling of the effluent stream and admixture with an oxygen-containing gas stream.

Liquid phase water from line 8 enters the heat exchange element 7 located within the cylindrical void volume of the dehydrogenation zone. The water is therein heated and preferably at least partially vaporized. The thus heated water flows through line 9 into a vapor-liquid separation zone 10 or steam drum. Unvaporized heated water may be withdrawn through line 25 as required. Steam is removed in line 11 and is admixed with a below ambient temperature high-purity oxygen stream from line 13 and is then passed into the dehydrogenation zone through line 12 and the distribution or sparger means 14. The oxygen thereby becomes admixed into the downward passing effluent of the dehydrogenation catalyst bed 6.

The now relatively cool admixture of reactants and oxygen passes into a cylindrical bed 15 of oxidation catalyst. This catalyst promotes the selective combustion or oxidation of the hydrogen released in the bed of dehydrogenation catalyst to thereby consume the hydrogen and release heat. By controlling the amount of oxygen which is added through line 12, the extent to which the total amount of available hydrogen is combusted within bed 15 may also be controlled. This control is preferably performed on the basis of a temperature measurement taken at the outlet of the bed of oxidation catalyst. This control method may therefore be employed to regulate the outlet temperature of the oxidation catalyst bed effluent stream, which is the temperature of the reactants being charged to the bed 16 of dehydrogenation catalyst. The rate of oxygen addition through line 12 is therefore preferably controlled on the basis of the preferred inlet temperature to the cylindrical catalyst bed 16. As the reactants enter and flow through the dehydrogenation catalyst of bed 16, an additional amount of ethylbenzene is converted to styrene and an additional amount of hydrogen is produced. The reactants are also cooled by the endothermic dehydrogenation reaction.

The effluent of the dehydrogenation catalyst bed 16 emerges into a cylindrical void volume 24 and is therein admixed with a relatively cold stream of oxygen-containing gas which is discharged from the distributor means 20. This oxygen-containing gas comprises ambient air from line 17 which is passed through a drier means 18 for the removal of excessive atmospheric moisture and is then passed into a cooler 19 wherein by indirect heat exchange against a low temperature cooling fluid the air is cooled to a temperature which is substantially below the ambient temperature. Drier 18 may be required to prevent condensation and/or solidification of atmospheric water vapor in cooler 19. The cooled air is then passed into the dehydrogenation zone by way of the distributor 20. The rate of flow of the air through line 17 is again preferably controlled on the basis at least one temperature measurement including a temperature taken at or near the reactant exit from the bed 21 of oxidation catalyst. The ambient air could also be cooled by admixture with cold oxygen-rich gas which is cold due to being depressured or due to the use of cyrogenic storage or cyrogenic separation.

The admixture of the descending reactants and the relatively cold oxygen enters and passes through the cylindrical bed of oxidation catalyst 21 wherein it is heated by the combustion of hydrogen. The reactants are thereby heated to the desired inlet temperature of the bed 22 of dehydrogenation catalyst such that the additional desired amount of dehydrogenation occurs within this catalyst bed as the reactants pass downward. The reactants finally emerge from the lower surface of the catalyst bed 22 into a collection chamber at the bottom of the dehydrogenation zone before withdrawal through line 5 and passage to the appropriate product recovery facilities such as described below. The effluent stream carried by line 5 will comprise an admixture of the residual unconverted ethylbenzene, steam from line 2 and which is formed within the dehydrogenation zone by the combustion of hydrogen, ethylbenzene, hydrogen, and reaction by-products including a small amount of light ends material, toluene and benzene.

This presentation of one embodiment of the invention has been simplified by not including a description of those pieces of commonly used process equipment, such as other control systems, pumps, heat exchangers, etc. which are employed in the operation of the process but are not necessary for a description of the operation or construction of the subject invention. This presentation of certain embodiments of the invention is not intended to preclude from the scope of the invention those other embodiments set out herein or which are the result of normal and expected modification and variation to those embodiments.

The overall structure of the dehydrogenation zone is also subject to extensive variation in addition to the variations of the control system. For instance, a complex grid of piping having a circular or branching structure could be employed for the distribution of the oxygen-containing gas stream within the void volume 23 instead of the single horizontal conduit having a multiplicity of outlet nozzles as shown in the drawing. It is also possible to place various elements within the void volumes for the purpose of admixing the gases emanating from the dehydrogenation catalyst beds with the oxygen-containing gas stream or to ensure vaporization of liquid phase coolants prior to entrance into downstream catalyst beds. However, the utilization of these mixing devices is not preferred as they tend to increase the cost of the apparatus and may increase the pressure drop through the process, which is undesirable. An adequate degree of mixing can be achieved by the proper design and selection of the gas distribution means.

The structure of the overall dehydrogenation zone may also be varied by changing the type of catalyst bed which is employed. For instance, radial flow through annular catalyst beds may be employed instead of the vertical flow through cylindrical catalyst beds depicted in the drawing. It is to be noted that with a radial flow embodiment of the invention the beds of dehydrogenation catalyst and oxidation catalyst may be concentrically located at the same elevation within the vessel. Either the oxidation catalyst or the dehydrogenation catalyst may be located in the outer bed of this arrangement. The gas flow would then pass through cylindrical center pipe regions located in the middle of the radial flow catalyst beds and through annular gas collection and distribution void volumes located between the outer surface of the catalyst beds and the inner wall of the vessel. Variation is also possible in the number of beds of catalyst which may be employed within the dehydrogenation process. For instance, the dehydrogenation process could employ two separate beds of dehydrogenation catalyst and one bed of oxidation catalyst, or four beds of dehydrogenation catalyst and three beds of oxidation catalyst may be employed. A separate oxygen-containing gas stream would be injected into the gas flow immediately upstream of each bed of oxidation catalyst.

One embodiment of the invention may accordingly be characterized as a hydrocarbon dehydrogenation process which comprises passing a feed stream comprising a $C_4$-plus feed hydrocarbon into a dehydrogenation zone and through a first bed of dehydrogenation catalyst maintained at dehydrogenation conditions and producing a first dehydrogenation zone effluent stream comprising hydrogen, the $C_4$-plus feed hydrocarbon and a $C_4$-plus less-saturated product hydrocarbon; forming a reduced temperature oxidation catalyst bed feed stream comprising an admixture of a below ambient temperature oxygen-containing stream and the first dehydrogenation zone effluent stream; passing the oxidation catalyst bed feed stream through a bed of hydrogen selective oxidation catalyst and producing an oxidation zone effluent stream; passing the oxidation zone effluent stream through a second bed of dehydrogenation catalyst maintained at dehydrogenation conditions and producing a second dehydrogenation zone effluent stream which comprises the product hydrocarbon; and recovering the product hydrocarbon.

The total amount of dehydrogenation catalyst employed in the process may be divided into ten or more separate beds, but the dehydrogenation zone preferably comprises two or three catalyst beds with means for the intermediate addition and admixture of any added steam and the oxygen supply steams. Suitable systems for this may be patterned after those presented in U.S. Pat. Nos. 3,498,755; 3,515,763; and 3,751,232. The catalyst beds may be contained in separate reaction vessels or they may be enclosed within a larger overall vessel or structure. The use of radial flow annular catalyst beds in a stacked configuration in a single overall vessel is sometimes preferred although the invention can be used with vertical flow in cylindrical beds as shown in the drawing.

Dehydrogenation catalysts generally consist of one or more metallic components selected from Groups VI and VIII of the Periodic Table. One typical catalyst for the dehydrogenation of alkylaromatics comprises 85% by weight ferric oxide, 2% chromia, 12% potassium hydroxide and 1% sodium hydroxide. A second dehydrogenation catalyst, which is used commerically, consists of 87–90% ferric oxide, 2–3% chromium oxide and from 8–10% potassium oxide. A third typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt. % iron oxide as an active catalytic agent, from about 1–8 wt. % zinc or copper oxide, about 0.5–50 wt. % of an alkali promoter, and from about 1–5 wt. % chromic oxide as a stabilizer and a binding agent. U.S. Pat. No. 4,467,046 also describes a catalyst for the dehydrogenation of ethylbenzene in the presence of steam. This catalyst contains 15 to 30 wt. % potassium oxide, 2 to 8% cerium oxide, 1.5 to 6% molybdenum oxide, 1 to 4% calcium carbonate, with the balance iron oxide.

Dehydrogenation conditions in general include a temperature of about 538 degrees to 750 degrees C (1000 degrees–1382 degrees F.) and preferably about 565 degrees to about 675 degrees C. (1050 degrees F.). The temperature required for efficient operation of any specific dehydrogenation process will depend on the feed hydrocarbon and the activity of the catalyst employed. The pressure maintained within the dehydrogenation zone may range from about 100 to about 750 mm Hg, with a preferred range of pressures being from 250 to 700 mm Hg. The operating pressure within the dehydrogenation zone is measured at the inlet, midsection, and outlet of the zone to thereby provide an approximately average pressure. The combined feed stream is charged to the dehydrogenation zone at a liquid hourly space velocity, based on liquid hydrocarbon charge at 60 degrees F. (15.6 degrees C.), of about 0.1 to about 2.0 $hr^{-1}$, and preferably from 0.2 to 1.0 $hr^{-1}$.

The alkylaromatic hydrocarbon to be dehydrogenated is preferably admixed with superheated steam to counteract the temperature lowering effect of the endothermic dehydrogenation reaction. The presence of steam has also been described as benefiting the stability of the dehydrogenation catalyst by preventing the accumulation of carbon deposits. Preferably, the steam is admixed with the other components of the feed stream at a rate of about 0.5 to about 1.5 pound of steam per pound of feed hydrocarbon. Other quantities of steam may be added after one or more subsequent beds if desired. However, the dehydrogenation zone effluent stream should contain less than about 3 pounds of steam per pound of product hydrocarbon and preferably less than 2 pounds of steam per pound of product hydrocarbon.

The effluent stream removed from the overall dehydrogenation zone is normally heat exchanged for the purpose of lowering its temperature for the recovery of heat. The effluent stream may be heat exchanged against a stream of steam, a reactant stream of this or another process or used as a heat source for fractionation, etc. Commercially, the effluent stream is often passed through several heat exchangers thereby heating a number of different streams. This heat exchange is performed subject to the constraints set out above. The heat exchange performed downstream of the first compression means should cool the dehydrogenation zone effluent stream sufficiently to affect the condensation of at least 95 mole percent of the feed and product $C_6$-plus hydrocarbons and also at least 95 mole percent of the water vapor. The use of a quench zone to accomplish this condensation is not preferred. Essentially all of the styrene or other product hydrocarbon, most water and other readily condensible compounds present in the effluent stream are thereby converted to liquids. This produces a mixed phase stream which is passed into a phase separation vessel. This procedure allows the facile crude separation by decantation of the hydrocarbons from the water and hydrogen present in the effluent stream. The styrene present in the dehydrogenation zone effluent stream becomes part of a hydrocarbon stream which is withdrawn from the separation vessel and transferred to the proper separation facilities. Preferably, the styrene or other product hydrocarbon is recovered from the hydrocarbon stream by using one of the several fractionation systems known in the art. This fractionation will preferably yield a relatively pure stream of ethylbenzene, which is recycled, and an additional stream comprising benzene and toluene. These two aromatic hydrocarbons are by-products of the dehydrogenation reaction. They may be recycled in part as taught in U.S. Pat. No. 3,409,689 and British Pat. No. 1,238,602 or entirely rejected from the process. Styrene is recovered as a third stream, which is withdrawn from the process. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon 6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080; and 3,517,081.

The recovery of styrene through the use of fractionation is described in several references including U.S. Pat. No. 3,525,776. In this reference, the hydrocarbonaceous phase removed from the phase separation zone is passed into a first column referred to as a benzene-toluene column. This column is operated at a subatmospheric pressure to allow its operation at lower temperatures and hence reduce the rate of styrene polymerization. Various inhibitors such as elemental sulfur, 2,4-dinitrophenol or a mixture of N-nitroso diphenylamine and a dinitroso-o-cresol are injected into the column for this same purpose. Sulfur can also be introduced into this column by returning at least a portion of the high molecular weight material separated from the bottoms stream of a styrene purification column. A more detailed description of this is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream preferably contains at least 95 mole percent benzene and toluene. The bottoms of the benzene-toluene column is passed into a second fractionation column from which ethylbenzene is removed as an overhead product and recycled. The bottoms stream of this column is then purified to obtain the styrene. Product recovery techniques directed to the recovery of vinyltoluene via fractionation and the use of chemical additives to inhibit polymerization are described in U.S. Pat. Nos. 4,417,085 and 4,492,675. The use of inhibitors and alternative fractionation techniques for readily polymerizable vinyl aromatic compounds is also described in U.S. Pat. No. 4,469,558.

The oxygen consumed during the hydrogen combustion is preferably admixed into the reactant stream at the point of interstage heating as part of an oxygen supply stream. The oxygen supply stream may be air but is preferably a gas having a higher oxygen content than air. It is preferred that the oxygen supply stream has a nitrogen content less than 10 mole percent, with the use of substantially pure oxygen being highly preferred if it is economically viable. The preferred oxygen concentration in the oxygen supply stream is primarily a matter of economics and would be determined by a comparison of the advantage of having pure oxygen to the cost of obtaining the oxygen. The basic disadvantages of the presence of nitrogen are the dilution of the hydrogen-containing gas stream removed from the product separation vessel and the fact that the nitrogen passes through the dehydrogenation zone thereby increasing the pressure drop through the catalyst bed and the absolute pressure being maintained within the dehydrogenation zone. On the other hand, the presence of nitrogen favorably affects the equilibrium conversion level by acting as a diluent.

The oxidation catalyst employed in the subject process to promote the interstage hydrogen oxidation may be any commercially suitable catalyst which meets the required standards for stability and activity and which possesses high selectivity for the oxidation of hydrogen as compared with the oxidation of the feed or product hydrocarbon. That is, the oxidation catalyst must have a high selectivity for the oxidation of hydrogen with only small amounts of the feed or product hydrocarbon being oxidized. The oxidation catalyst will have a different composition than the dehydrogenation catalyst. The preferred oxidation catalyst comprises a Group VIII noble metal and a metal or metal cation which possesses a crystal ionic radius greater than 1.35 angstroms, with both of these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5.0 wt. % of the finished catalyst. The metal or metal cation having a radius greater than 1.35 angstroms is preferably chosen from Groups IA or IIA and is present in an amount equal to about 0.01 to about 20 wt. % of the finished catalyst. This component of the catalyst is preferably barium, but the use of other metals including rubidium or cesium is also contemplated.

The preferred solid support is alumina having a surface area between 1 and 300 m$^2$/g, an apparent bulk density of between about 0.2 and 1.5 g/cc, and an average pore size greater than 20 angstroms. The metal-containing components are preferably impregnated into solid particles of the solid support by immersion in an aqueous solution followed by drying and calcination at a temperature of from about 500 degrees to 600 degrees C. in air. The support may be in the form of spheres, pellets or extrudates. The total amount of oxidation catalyst present within the dehydrogenation zone is preferably less than 30 wt. % of the total amount of dehydrogenation catalyst and more preferably is between 5 and 15 wt. % of this total amount of dehydrogenation catalyst.

The conditions utilized during the contacting of the reactant streams with the different beds of oxidation catalyst will be set to a large extent by the previously referred to dehydrogenation conditions. The preferred outlet temperature of any bed of oxidation catalyst is the preferred inlet of the immediately downstream bed of dehydrogenation catalyst. The temperature rise across the oxidation catalyst bed should be adjusted to react at least 75 and preferably 85 percent of the hydrogen approaching this catalyst. The liquid hourly space velocity, based on the liquid hydrocarbon charge at standard conditions (60 degrees F.), is preferably between 4 and 20 hr$^{-1}$. It is preferred that substantially all of the oxygen which enters a bed of oxidation catalyst is consumed within that bed of oxidation catalyst and that the effluent stream of any bed of oxidation catalyst contains less than 0.1 mole percent oxygen.

The total moles of oxygen charged to the dehydrogenation zone is preferably more than 35% of the total moles of hydrogen available within the dehydrogenation zone for combustion and is therefore dependent on the conversion achieved in the dehydrogenation zone. This available hydrogen is the sum of any hydrogen recycled to the dehydrogenation zone and the hydrogen produced in all but the last bed of dehydrogenation catalyst. Preferably the oxygen charged to the dehydrogenation zone is equal to about 30 to 48 mole percent of the thus-defined available hydrogen. As used herein, the term "substantially all" is intended to indicate a major fraction of the indicated chemical compound(s) have been acted upon in the manner described, with this major fraction preferably being over 90 mole percent and more preferably over 95 mole percent. As previously mentioned, the subject process is not limited to the production of styrene and may be used to produce paramethylstyrene by dehydrogenation of ethyltoluene or for the production of other unsaturated product hydrocarbons such as acyclic $C_3$-$C_8$ olefins. The product hydrocarbon recovered from the process may therefore be propylene, a butylene or a mixture of butylenes, a heptene, etc.

I claim as my invention:

1. In a process for the catalytic dehydrogenation of a $C_3$-plus dehydrogenable hydrocarbon wherein a feed stream comprising a feed hydrocarbon is passed into a first bed of dehydrogenation catalyst maintained at dehydrogenation conditions and a dehydrogenation zone effluent stream comprising hydrogen, the feed hydrocarbon and a product hydrocarbon is produced, the dehydrogenation zone effluent stream and an oxygen-containing gas stream are admixed and passed into a separate bed of selective hydrogen oxidation catalyst maintained at oxidation promoting conditions and an oxidation zone effluent stream is produced, and the oxidation zone effluent stream is passed into a second bed of dehydrogenation catalyst; the improvement which comprises cooling the dehydrogenation zone effluent stream by direct or indirect heat exchange and increasing the amount of heating which is required in the bed of oxidation catalyst over that which would be necessary to achieve the same oxidation zone effluent stream temperature without said cooling.

2. The process of claim 1 further characterized in that the cooling of the dehydrogenation zone effluent stream comprises the step of vaporizing water by indirect heat exchange.

3. The process of claim 2 further characterized in that the cooling of the dehydrogenation zone effluent stream comprises the step of cooling the oxygen-containing gas stream to a below ambient temperature prior to passage into the dehydrogenation zone.

4. The process of claim 1 further characterized in that the cooling of the dehydrogenation zone effluent stream comprises the step of vaporizing water by direct heat exchange within the dehydrogenation zone.

5. In a process for the catalytic dehydrogenation of a $C_3$-plus dehydrogenable hydrocarbon wherein a feed stream comprising a feed hydrocarbon is passed into a first bed of dehydrogenation catalyst maintained at dehydrogenation conditions and a dehydrogenation zone effluent stream comprising hydrogen, the feed hydrocarbon and a product hydrocarbon is produced, the dehydrogenation zone effluent stream and an oxygen-containing gas stream are admixed and passed into a separate bed of selective hydrogen oxidation catalyst maintained at oxidation promoting conditions and an oxidation zone effluent stream is produced, and the oxidation zone effluent stream is passed into a second bed of dehydrogenation catalyst; the improvement which comprises increasing the amount of hydrogen which is consumed within the bed of oxidation catalyst without increasing the temperature of the oxidation zone effluent stream by decreasing the temperature of the admixture of the dehydrogenation zone effluent stream and the oxygen-containing gas stream through the use of a below ambient temperature oxygen-containing gas stream.

6. A process for the catalytic dehydrogenation of a dehydrogenatable $C_3$-plus feed hydrocarbon which comprises the steps of:
(a) passing a feed stream comprising the $C_3$-plus feed hydrocarbon into a dehydrogenation zone and through a first bed of dehydrogenation catalyst maintained at dehydrogenation conditions and producing a first dehydrogenation zone effluent stream comprising hydrogen, the $C_3$-plus feed hydrocarbon and a $C_3$-plus product hydrocarbon;
(b) forming a reduced temperature oxidation catalyst bed feed stream by admixing a below ambient temperature oxygen-containing stream with the first dehydrogenation zone effluent stream;
(c) passing the oxidation catalyst bed feed stream through a bed of hydrogen selective oxidation catalyst and producing an oxidation zone effluent stream;
(d) passing the oxidation zone effluent stream through a second bed of dehydrogenation catalyst maintained at dehydrogenation conditions and producing a second dehydrogenation zone effluent stream which comprises the product hydrocarbon; and
(e) recovering the product hydrocarbon.

7. The process of claim 6 further characterized in that the oxygen-containing stream comprises air which has been cooled after collection from the atmosphere.

8. The process of claim 6 further characterized in that the feed hydrocarbon is an alkylaromatic hydrocarbon.

9. The process of claim 8 further characterized in that the feed hydrocarbon is ethylbenzene.

10. A process for the catalytic dehydrogenation of a dehydrogenatable $C_3$-plus feed hydrocarbon which comprises the steps of:
(a) passing a feed stream comprising the $C_3$-plus feed hydrocarbon into a dehydrogenation zone and through a first bed of dehydrogenation catalyst maintained at dehydrogenation conditions and producing a first dehydrogenation zone effluent stream comprising hydrogen, the $C_3$-plus feed hydrocarbon and a $C_3$-plus product hydrocarbon;
(b) cooling the dehydrogenation zone effluent stream by indirect heat exchange, and admixing an oxygen-containing gas stream into the dehydrogenation zone effluent stream;
(c) passing the dehydrogenation zone effluent stream into a separate bed of hydrogen selective oxidation catalyst and producing an oxidation zone effluent stream;
(d) passing the oxidation zone effluent stream through a second bed of dehydrogenation catalyst maintained at dehydrogenation conditions and producing a second dehydrogenation zone effluent stream which comprises the product hydrocarbon; and
(e) recovering the product hydrocarbon.

11. The process of claim 10 further characterized in that the indirect heat exchange of step (b) produces steam which is passed into the bed of oxidation catalyst.

12. The process of claim 10 further characterized in that the indirect heat exchange of step (b) is used to heat liquid phase water.

13. The process of claim 10 further characterized in that the oxygen-containing gas stream comprises air having a below ambient temperature.

14. The process of claim 10 further characterized in that the feed hydrocarbon is an alkylaromatic hydrocarbon.

15. The process of claim 14 further characterized in that the feed hydrocarbon is ethyltoluene.

16. The process of claim 14 further characterized in that the feed hydrocarbon is ethylbenzene.

17. The process of claim 11 further characterized in that the feed hydrocarbon is propane.

18. The proceses of claim 11 further characterized in that the feed hydrocarbon is butane.

* * * * *